(12) United States Patent
Zollinger

(10) Patent No.: US 9,861,804 B2
(45) Date of Patent: Jan. 9, 2018

(54) COMPRESSIBLE NEEDLELESS VALVE ASSEMBLY

(71) Applicant: CareFusion 303, Inc., San Diego, CA (US)

(72) Inventor: Christopher Zollinger, Chino Hills, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 14/887,144

(22) Filed: Oct. 19, 2015

(65) Prior Publication Data

US 2016/0038730 A1 Feb. 11, 2016

Related U.S. Application Data

(63) Continuation of application No. 13/673,971, filed on Nov. 9, 2012, now Pat. No. 9,162,029.

(51) Int. Cl.
*A61M 39/02* (2006.01)
*A61M 39/10* (2006.01)
(Continued)

(52) U.S. Cl.
CPC .............. *A61M 39/22* (2013.01); *A61M 5/31* (2013.01); *A61M 39/02* (2013.01);
(Continued)

(58) Field of Classification Search
CPC .. A61M 2039/0202; A61M 2039/0205; A61M 2039/2406; A61M 2039/263; A61M 2039/261; A61M 2039/246; A61M 2039/2446; A61M 2039/2433; A61M 39/02; A61M 39/10; A61M 39/22; A61M 39/00; A61M 39/0208; A61M 39/04;
(Continued)

(56) References Cited

U.S. PATENT DOCUMENTS 5,215,538 A * 6/1993 Larkin .................. A61M 39/26
137/516.13
5,360,413 A 11/1994 Leason et al.
(Continued)

FOREIGN PATENT DOCUMENTS

CN 1764798 A 4/2006
CN 102686265 A 9/2012
(Continued)

OTHER PUBLICATIONS

Chinese Office Action for Application No. 201380064240.1, dated Jan. 10, 2017, 6 pages excluding translation.
(Continued)

*Primary Examiner* — Mary McManmon
*Assistant Examiner* — Hailey K Do
(74) *Attorney, Agent, or Firm* — McDermott Will & Emery LLP

(57) ABSTRACT

A valve for a needleless valve system. The valve includes a body configured to be disposed in the needleless valve system and controlling fluid flow through the needleless valve system and wherein the body is tail-less. The body includes a continuous top surface, and a compression feature configured to control how the body is compressed to allow fluid flow through the needleless valve system.

16 Claims, 5 Drawing Sheets

(51) Int. Cl.
    *A61M 39/24*     (2006.01)
    *A61M 39/26*     (2006.01)
    *A61M 39/22*     (2006.01)
    *A61M 5/31*     (2006.01)
    *A61M 39/20*     (2006.01)

(52) U.S. Cl.
    CPC ........ *A61M 39/0208* (2013.01); *A61M 39/10* (2013.01); *A61M 39/105* (2013.01); *A61M 39/20* (2013.01); *A61M 39/26* (2013.01); *A61M 2039/2433* (2013.01)

(58) Field of Classification Search
    CPC ....... A61M 39/24; A61M 39/25; F16K 15/00; F16K 15/14; F16K 15/144; F16K 15/147; F16K 7/00; F16K 7/12; F16K 7/20
    USPC ............ 137/613, 614.05, 859, 843; 251/147, 251/149.1, 149.2, 149.6–149.9; 604/256
    See application file for complete search history.

(56) References Cited

U.S. PATENT DOCUMENTS

| | | | |
|---|---|---|---|
| 5,573,516 A | 11/1996 | Tyner | |
| 5,730,418 A | 3/1998 | Feith et al. | |
| 5,782,816 A * | 7/1998 | Werschmidt | A61M 39/02 137/903 |
| 6,855,138 B2 | 2/2005 | Tsai | |
| 8,708,976 B1 * | 4/2014 | Yeh | A61M 39/26 604/236 |
| 9,017,295 B2 * | 4/2015 | Pan | A61M 39/10 604/246 |
| 9,162,029 B2 * | 10/2015 | Zollinger | A61M 39/02 |
| 9,409,007 B2 * | 8/2016 | Yeh | A61M 39/22 |
| 2004/0195538 A1 | 10/2004 | Raines et al. | |
| 2005/0010177 A1 | 1/2005 | Tsai | |
| 2007/0260195 A1 | 11/2007 | Bartholomew et al. | |
| 2010/0234798 A1 | 9/2010 | Huang | |
| 2012/0059334 A1 * | 3/2012 | Pan | A61M 39/10 604/236 |
| 2013/0190684 A1 | 7/2013 | Panian et al. | |

FOREIGN PATENT DOCUMENTS

| | | | | |
|---|---|---|---|---|
| EP | 0629418 A2 * | 12/1994 | | A61M 39/26 |
| EP | 2815785 A1 * | 12/2014 | | A61M 39/045 |
| JP | S6045039 U | 3/1985 | | |
| JP | H10192415 A | 7/1998 | | |
| JP | 3166779 U | 3/2011 | | |
| WO | WO-2004/112866 A2 | 12/2004 | | |
| WO | WO 2009144599 A1 * | 12/2009 | | A61M 5/16804 |
| WO | WO-2011060384 A1 | 5/2011 | | |
| WO | WO-2013109586 A1 | 7/2013 | | |

OTHER PUBLICATIONS

Chinese Office Action for Application No. 201380064240.1, dated Sep. 11, 2017, 8 pages excluding translation.
Australian Examination Report No. 1 for Application No. 2013341543, dated Jul. 13, 2017, 4 pages.
Japanese Office Action for Application No. 2015-541825, dated Aug. 8, 2017, 3 pages excluding English translation.

* cited by examiner

COMPRESSIBLE NEEDLELESS VALVE ASSEMBLY

CROSS-REFERENCE TO RELATED APPLICATIONS

This application is a continuation of U.S. patent application Ser. No. 13/673,971, filed on Nov. 9, 2012, entitled "TAILLESS NEEDLELESS VALVE SYSTEM," the disclosure of which is incorporated herein by reference in its entirety.

BACKGROUND

A needleless valve system that includes a valve with a tail requires a housing that can encompass the tail. Accordingly, additional force is required to compress the tail and additional fluid is required to prime and/or flush the housing that encompasses the tail.

BRIEF DESCRIPTION

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, and components have not been described in detail as not to unnecessarily obscure aspects of the present embodiments.

Figure 1A:
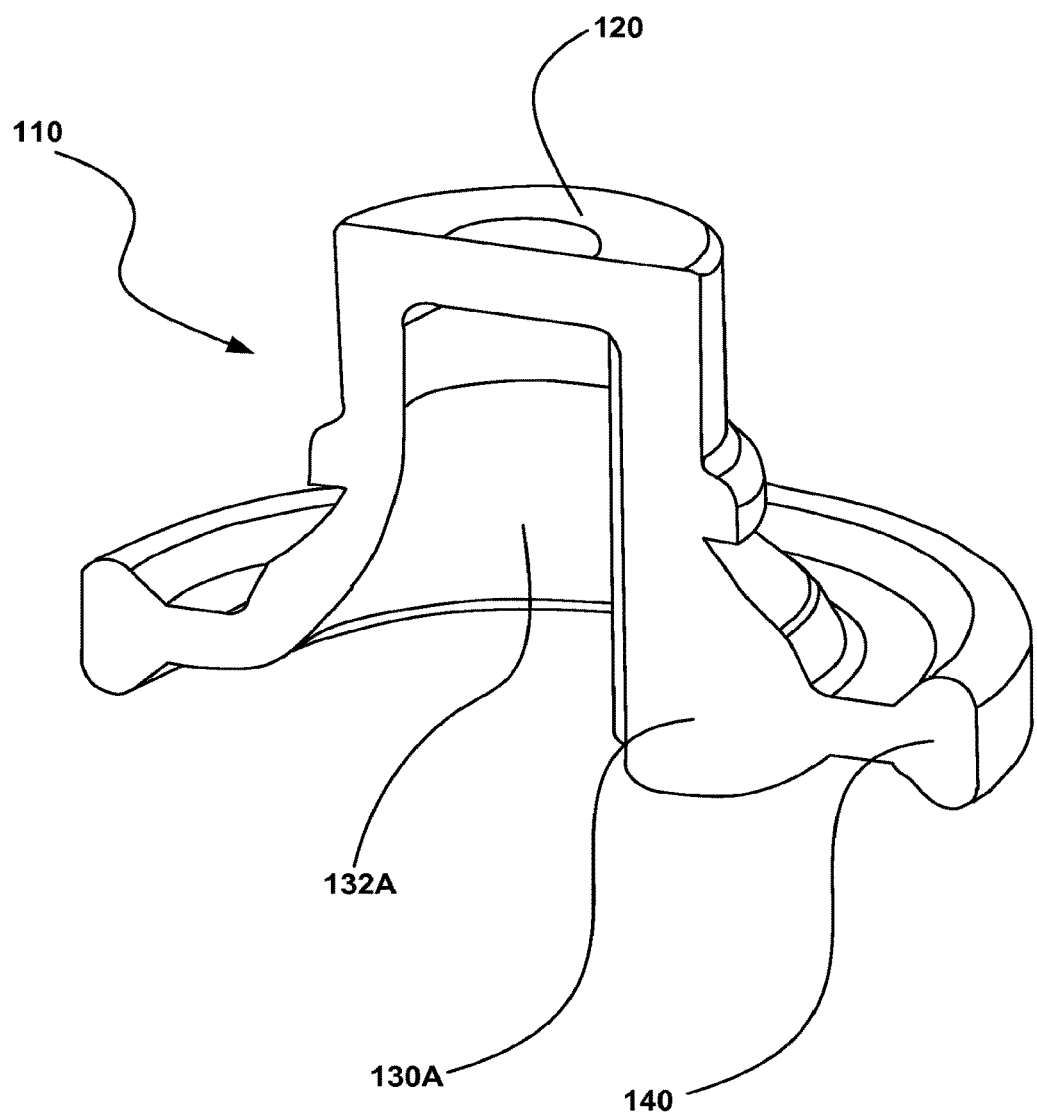
FIGS. 1A-B depicts embodiments of tail-less valves.
Figure 1B:
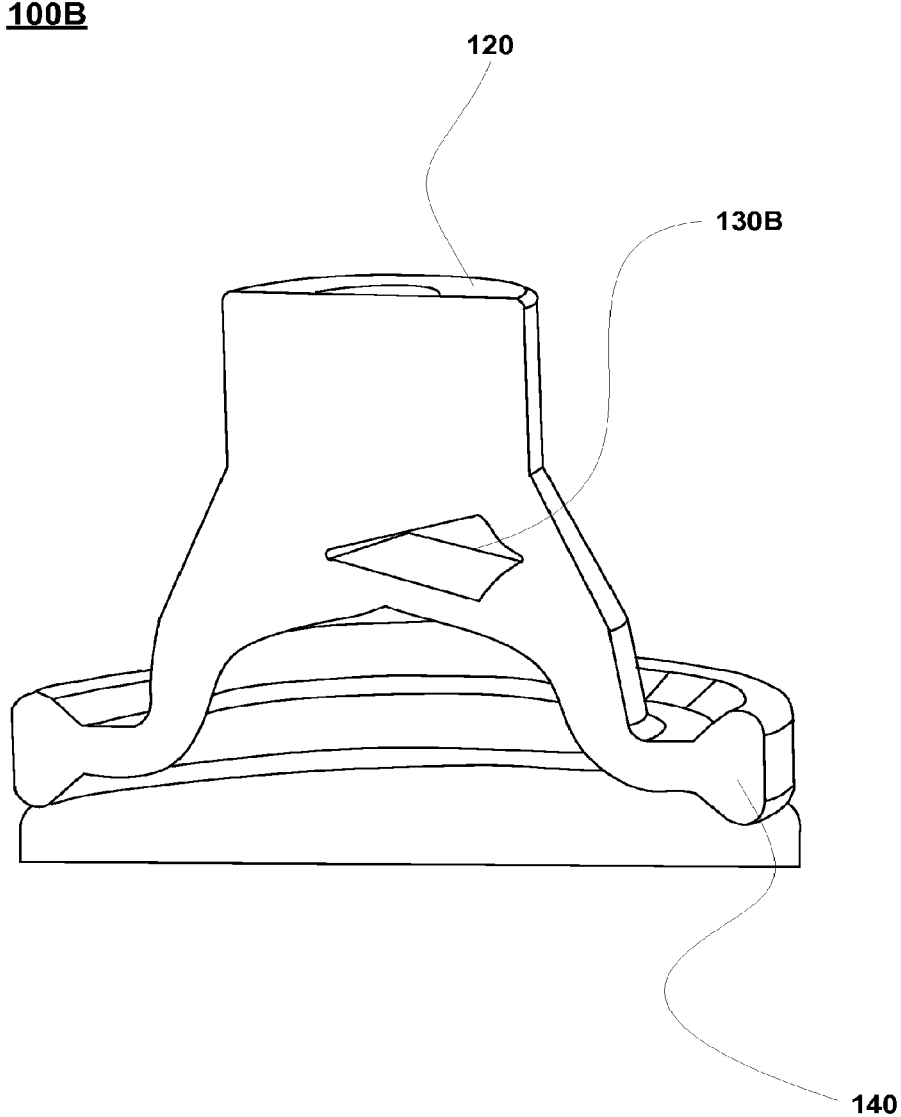
Figure 2:
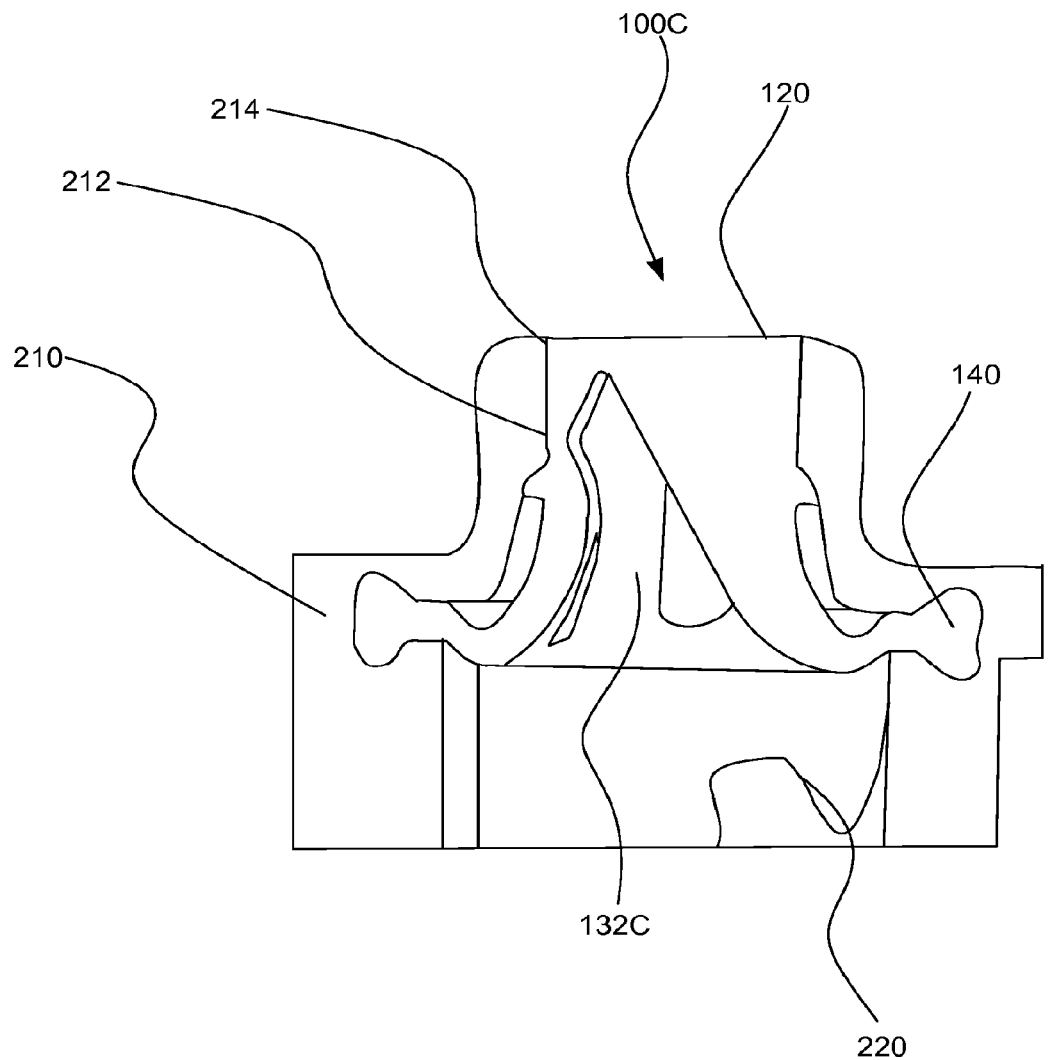
FIGS. 2-4 depicts embodiments of needleless valve systems.
The drawings referred to in this description should be understood as not being drawn to scale except if specifically noted.

FIGS. 1A-2 depicts an isometric cross-sectional view of various embodiments of valves 100A-C, respectively. Specifically, FIG. 2 depicts an isometric cross-sectional view of a needleless valve assembly 200.

Valves 100A-C are similar in structure and functionality. For clarity and brevity, the description herein, will focus on valve 100A. Valve 100A and other valves described herein can also be described as a valve plug, piston, etc. Valve 100A is configured to be utilized in a needleless valve system, which will be described in further detail below.

Valve 100A is tail-less. That is valve 100A does not include a tail that protrudes down from body 110.

In contrast, in conventional valves for a needleless valve system, the valve includes a tail portion that physically contacts the valve housing. In particular, the tail is compressed by a needleless luer. When the luer is removed from the housing, the tail relaxes to its original position and urges the valve back into a sealed position.

Because valve 100A is tail-less, less material is required to manufacture the valve and also less material manufacture the housing (e.g., housing 210) that surrounds valve. As a result, cost is reduced to manufacture the tail-less valve and associated needleless valve assembly.

Moreover, less force is required to deform the valve into an unsealed position as compared to a conventional valve that includes a tail.

Additionally, the height of the valve is reduced. As a result, the housing to encase the valve is also reduced. As such, the housing may include a lower volume (e.g., volume 330) as compared to housings of conventional needleless valve assemblies. Therefore, less fluid is required to properly prime and/or flush the housing.

Valve 100A includes, among other things, body 110, top surface 120, compression feature 130A, internal cavity 132A and retaining flange 140.

Top surface 120 is configured to seal a port of a housing, which will be described in detail below. Top surface 120 is continuous and does not include (or does not require) any broken portions. For example, top surface 120 is a continuous feature that does not include a slit, cut, hole, etc. In particular, top surface 120 does not require a split septum.

Top surface 120 is a smooth unbroken surface. As such, when top surface is swabbed, pathogens are readily removed and the surface is properly sanitized.

Retaining flange 140 is for retaining valve 100A within housing 210. It should be appreciated that valve 100A may be retained within the housing by various retaining features and mechanisms that are compatible for proper and secure retention.

Compression feature 130A is a wall with a thickness that is greater, as compared, to the wall thickness proximate the thick wall. It should be noted that a compression feature, as described herein, is any physical feature or combination of physical features that controls or directs the compression/collapse of the valve. For example, compression feature 130A, because it has a greater wall thickness, will cause body 110 to compress in an area with a thinner wall thickness (or an area away from compression feature 130A). Also, the combination of compression feature 130A and cavity 132 may facilitate in the controlled location of the compression of valve 100A.

Compression feature 130B is a through hole or cavity through the entire body. As such, valve 110B will readily collapse or compress in the area of compression feature 130B.

Compression feature 132C is an amorphous and asymmetrical cavity extending from a bottom surface up towards top surface 120. As such, valve 110C will readily collapse or compress in the area of compression feature 132C.

It should be appreciated that various compression features can be, but are not limited to, asymmetric along a center cross-section of said body, off-set along a center cross-section of said body, etc.

FIG. 2 depicts needleless valve assembly 200 in a closed or sealed position. That is, valve 100C, in a relaxed and natural position, is seated in housing 210 via retaining flange 140. In particular, the peripheral outer surface of valve 100C seals against inner wall 212 such that port 214 is fluidly sealed. That is, fluid is unable to pass through port 214 (in either direction).

In various embodiments, needleless valve assembly 200 can be attached or fluidly connected to a catheter or a stop-cock. Needleless valve assembly 200 may be integrated with other valving mechansims, such as a stop cock.

Valves 100A-C may be comprised of any material that is conducive for proper sealing and controlled deformation and an ability to naturally spring back to its natural position. For example, valves may be comprised of silicone.

Figure 3:
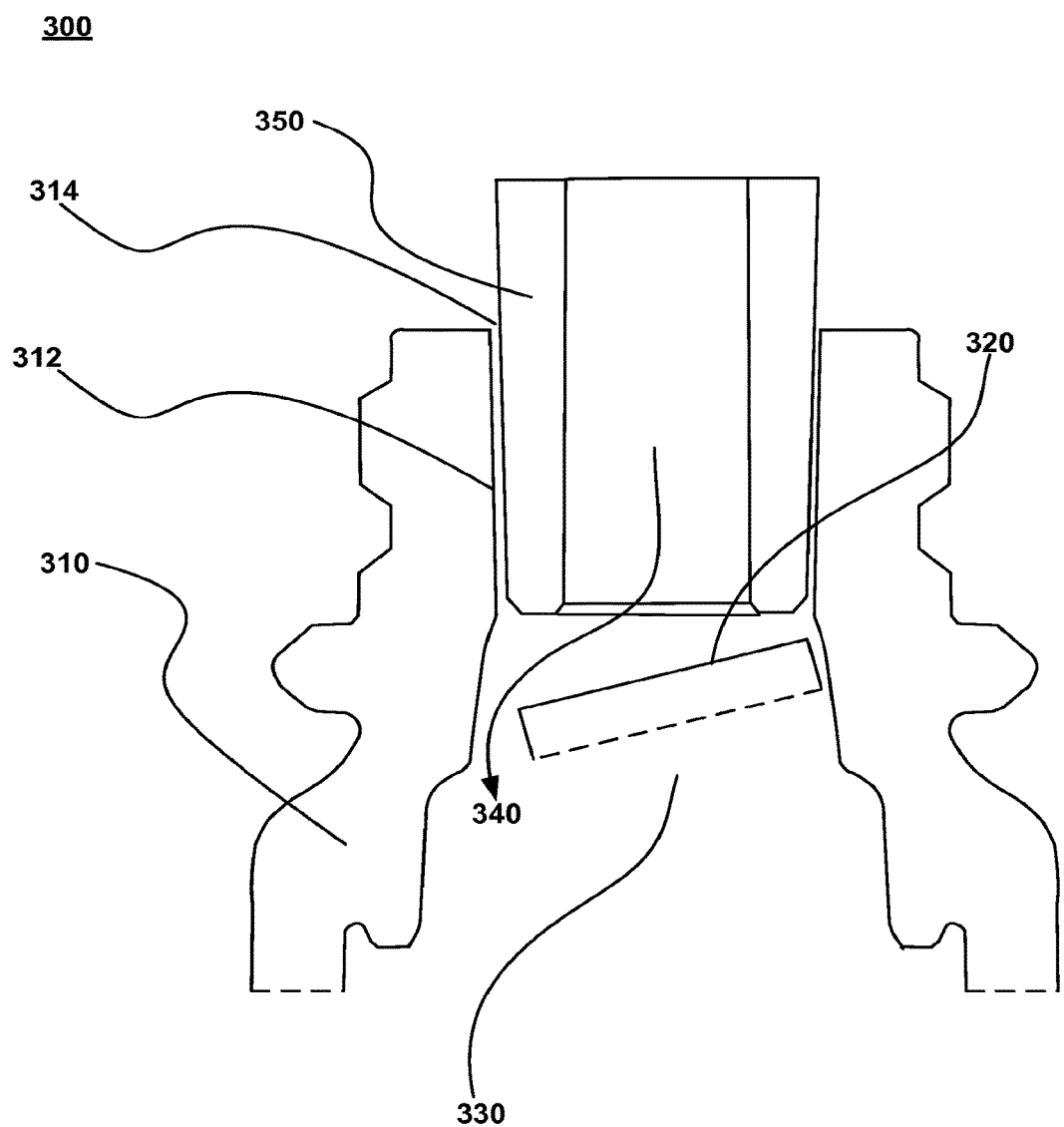

FIG. 3 depicts a cross-sectional view of needleless valve assembly 300. Needleless device 350 (e.g., a needleless syringe) is forced into port 314 such the valve (e.g., valves 100A-C) is deformed. For clarity and brevity, the displacement of top surface 320 is shown during unsealing of port 314. However, the compressed or deformed body of the valve within housing 310 is not shown.

Needleless device 350 displaces the head of valve downward along inner wall 312. Once top surface 320 is positioned within shoulder 316 (which has a greater diameter than the diameter at inner wall 312) then the seal is broken and fluid flow is able to occur. In one embodiment, top surface 320 is planar and/or tilted (at an angle with respect to the tip of the needleless device) based on the compression feature (e.g., compression features 130A-C) of the body of the valve.

Fluid is able to flow in direction 340 from needleless device 350, around top surface 320 and through housing 310 to the patient. It should be appreciated that housing 310 and/or the valve include ports or channels (not shown) that allow the fluid to pass entirely through needleless valve assembly 300.

In one embodiment, fluid flow may occur in the opposite direction. For example, blood is drawn from the patient into volume 330 around the valve and top surface 320 into a needleless syringe.

When needleless device 350 is removed from needleless valve assembly 300, the valve relaxes to its original position such that top surface reseals port 314.

Figure 4:
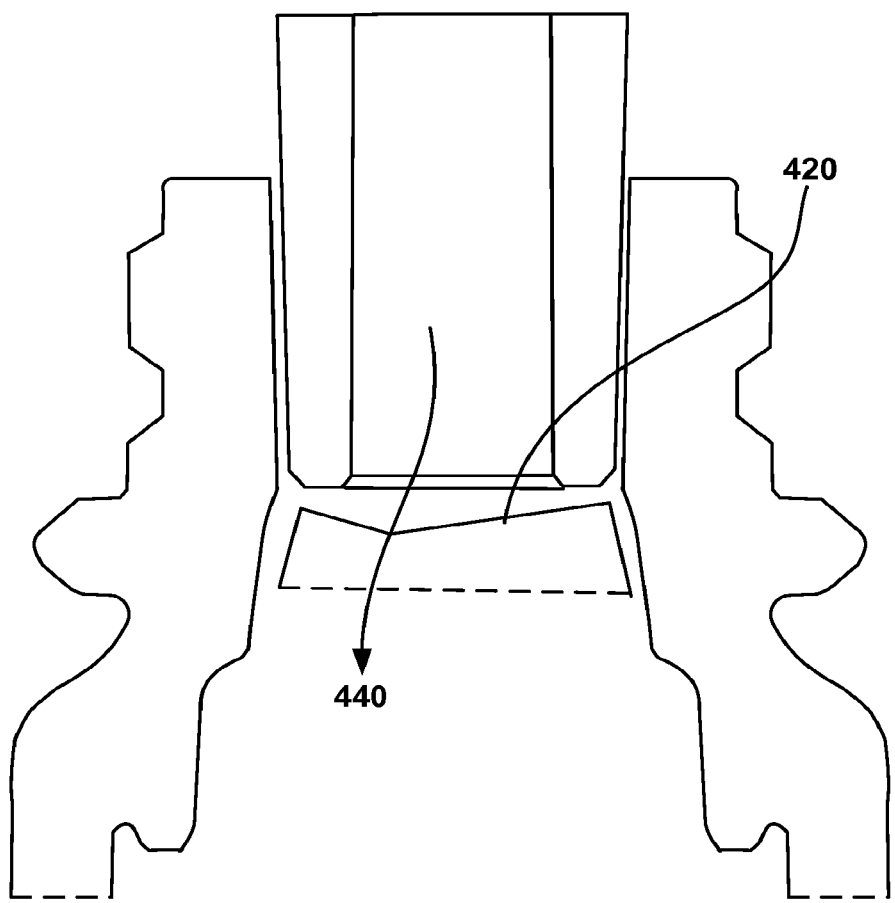

FIG. 4 depicts a cross-sectional view of needleless valve assembly 400. Needleless valve assembly 400 is similar to needleless valve assembly 300, as described above. In one embodiment, top surface 420 is deformed in a "V-shape" when the needleless device pushes down on top surface 420 and the valve is deformed such that the port is unsealed. In particular, top surface 420 is deformed into the "V-shape" based on the compression feature (e.g., compression features 130A-C) of the body of the valve. As such, fluid is able to flow in direction 440 from the needleless device, around top surface 420 and through the housing to the patient. It should be appreciated that the housing and/or the valve include ports or channels (not shown) that allow the fluid to pass entirely through needleless valve assembly 400.

In various embodiments, top surface 420 can be deformed into any non-planar shape such the seal is broken and fluid is able to flow through needleless valve assembly 400.

It should be appreciated that embodiments, as described herein, can be utilized or implemented alone or in combination with one another. While the present invention has been described in particular embodiments, it should be appreciated that the present invention should not be construed as limited by such embodiments, but rather construed according to the following claims.

The invention claimed is:

1. A compressible needleless valve assembly comprising:
a valve configured to be disposed in the compressible needleless valve assembly and for controlling a fluid flow through the compressible needleless valve assembly, the valve comprising:
a head having a distal end and a proximal end, the distal end of the head comprising a continuous top surface, wherein the continuous top surface is non-planar during the fluid flow through the compressible needleless valve assembly; and
an annular skirt coupled to the proximal end of the head, the skirt comprising (i) a retaining flange at a proximal most end of the valve, extending radially outward from a central longitudinal axis of the valve, and (ii) a compression feature extending radially inward from, and discontinuous around, an inner surface of the skirt such that a wall thickness of the skirt is greater at the compression feature than at an opposite side of the skirt, the retaining flange and the compression feature positioned coplanar along the central longitudinal axis, wherein the compression feature is configured to control how the valve is compressed to permit the fluid flow through the compressible needleless valve assembly.

2. The valve of claim 1, wherein the continuous top surface does not require a slit.

3. The valve of claim 1, wherein the compression feature is asymmetric.

4. The valve of claim 1, wherein the compression feature is asymmetric along a center cross-section of the valve.

5. The valve of claim 1, wherein the compression feature is off-set along a center cross-section of the valve.

6. The valve of claim 1, wherein a portion of the valve is hollow.

7. The valve of claim 1, wherein the compression feature further comprises a cavity extending entirely through the valve.

8. The valve of claim 7, wherein the cavity extends through the valve, between the distal end of the head and the proximal end of the head.

9. A compressible needleless valve assembly comprising:
a housing comprising a fluid port; and
a valve disposed in the housing, the valve comprising:
a head having a distal end and a proximal end, the distal end of the head comprising a continuous top surface, wherein the continuous top surface is non-planar during the fluid flow through the compressible needleless valve assembly; and
an annular skirt coupled to the proximal end of the head, the skirt comprising (i) a retaining flange at a proximal most end of the valve, extending radially outward from a central longitudinal axis of the valve, and (ii) a compression feature extending radially inward from, and discontinuous around, an inner surface of the skirt such that a wall thickness of the skirt is greater at the compression feature than at an opposite side of the skirt, the retaining flange and the compression feature positioned coplanar along the central longitudinal axis, wherein the compression feature is configured to control how the valve is compressed to permit the fluid flow through the compressible needleless valve assembly.

10. The compressible needleless valve assembly of claim 9, wherein the continuous top surface is tilted with respect to a top surface of the housing during the fluid flow through the compressible needleless valve assembly.

11. The compressible needleless valve assembly of claim 9, wherein the continuous top surface does not require a slit.

12. The compressible needleless valve assembly of claim 9, wherein the compression feature further comprises a cavity extending entirely through the valve.

13. The valve of claim 12, wherein the cavity extends through the valve, between the distal end of the head and the proximal end of the head.

14. The compressible needleless valve assembly of claim 9, wherein the compression feature is asymmetric.

15. The compressible needleless valve assembly of claim 9, wherein the compression feature is asymmetric along a cross-section of the valve.

16. The compressible needleless valve assembly of claim 9, wherein a portion of the valve is hollow.

\* \* \* \* \*